United States Patent [19]

Lardy

[11] Patent Number: 5,807,848
[45] Date of Patent: Sep. 15, 1998

[54] USE OF DEHYDROEPEIANDROSTERONE-3-CARBOXYLATES TO CONTROL BODY WEIGHT

[75] Inventor: Henry A. Lardy, Madison, Wis.

[73] Assignee: Humanetics Corporation, St. Louis Park, Minn.

[21] Appl. No.: 771,335

[22] Filed: Dec. 16, 1996

Related U.S. Application Data

[63] Continuation-in-part of Ser. No. 189,917, Feb. 2, 1994, Pat. No. 5,585,371, which is a continuation-in-part of Ser. No. 922,850, Jul. 31, 1992, Pat. No. 5,292,730, which is a continuation-in-part of Ser. No. 867,288, Apr. 10, 1992, Pat. No. 5,296,481, which is a continuation of Ser. No. 575,156, Aug. 29, 1990, abandoned.

[51] Int. Cl.$^6$ .................................................. A61K 31/56
[52] U.S. Cl. .............................................. 514/171; 514/178
[58] Field of Search ...................................... 514/171, 178

[56] References Cited

U.S. PATENT DOCUMENTS 5,296,481  3/1994  Partridge et al. ........................ 514/178
5,585,371  12/1996  Lardy ...................................... 514/171

*Primary Examiner*—Theodore J. Criares
*Attorney, Agent, or Firm*—Michael S. Sherrill

[57] ABSTRACT

Method of prophylactically averting weight gain, promoting weight loss and treating obesity with a family of thermogenic steroids. Such steroids include substantially pure Δ5 Androstene-17-ones having an ester of a saturated, unbranched $C_{2-24}$ monocarboxylic acid attached at the 3β-position of the base steroid ring.

39 Claims, No Drawings ns
USE OF DEHYDROEPEIANDROSTERONE-3-CARBOXYLATES TO CONTROL BODY WEIGHT

This application is a continuation-in-part of U.S. patent application Ser. No. 08/189,917 filed 2, Feb. 1994, U.S. Pat. No. 5,585,371 issued 17 Dec. 1996, which is a continuation-in-part of U.S. patent application Ser. No. 07/922,850 filed 31 Jul. 1992, now issued as U.S. Pat. No. 5,292,730, which is a continuation-in-part of U.S. patent application Ser. No. 07/867,288 filed 10 Apr. 1992, now issued as U.S. Pat. No. 5,296,481, which is a continuation of U.S. patent application Ser. No. 07/575,156 filed 29 Aug. 1990, now abandoned.

FIELD OF THE INVENTION

The invention relates to steroids and the use of steroids for promoting weight maintenance and/or weight loss (hereinafter referenced collectively as "weight control").

BACKGROUND

Persons throughout the world, especially those living in the United States of America, are actively involved in efforts to improve their health by losing weight. Many others are interested in simply avoiding any weight gain. This interest has reached such levels that an entire "weight loss" industry has developed. A variety of pharmacological agents, such as anorectic agents, as well as a number of dietary weight loss programs, have been developed to assist those seeking to lose weight or avoid gaining weight.

Despite the wide variety of pharmacological weight control agents available upon the market, efforts continue to locate different pharmacological agents which provide the desired weight controlling effect without the adverse side effects associated with many of the known weight loss agents.

SUMMARY OF THE INVENTION

I have discovered a family of steroids which are biologically effective for prophylactically averting weight gain, promoting weight loss and treating obesity. The steroids are Δ5 Androstene-17-ones having an ester of a saturated, unbranched $C_{2-24}$ monocarboxylic acid attached at the 3β-position of the base steroid ring (hereinafter referenced collectively as Δ5 Androstene-3β-carboxylate-17-ones). Specific Δ5 Androstene-3β-carboxylate-17-ones possessing the described weight control attribute include Δ5 Androstene-3β-hemisuccinate-17-one, Δ5 Androstene-3β-propionate-17-one, Δ5 Androstene-3β-butyrate-17-one, Δ5 Androstene-3β-laurate-17-one and Δ5 Androstene-3β-palmitate-17-one.

These steroids can be synthesized in substantially pure form and compounded into pharmaceutical compositions by incorporating the steroid into a pharmaceutically acceptable carrier.

DETAILED DESCRIPTION OF THE INVENTION INCLUDING A BEST MODE

The Steroids

I have identified a family of steroids effective for prophylactically averting weight gain, promoting weight loss and treating obesity. The steroids are Δ5 Androstenes with an ester of a saturated, unbranched $C_{2-24}$ monocarboxylic acid attached at the 3β-position and a keto group attached at the 17-position (hereinafter referenced collectively as Δ5 Androstene-3Δ-carboxylate-17-ones). Such steroids may be synthesized by known techniques and are commercially available from various sources. For example, Δ5 Androstene-3β-hemisuccinate-17-one and Δ5 Androstene-3β-propionate-17-one are available from Steraloids, Inc. of Wilton, N.H.

Specific Δ5 Androstene-3β-carboxylate-17-ones possessing the described weight control attribute have been synthesized and tested for thermogenic activity. These steroids include Δ5 Androstene-3β-hemisuccinate-17-one, Δ5 Androstene-3β-propionate- 17-one, Δ5 Androstene-3β-butyrate-17-one, Δ5 Androstene-3β-laurate-17-one and Δ5 Androstene-3βpalmitate-17-one.

Administration

Administration Route

The substantially pure steroids can be administered by virtually any of the commonly accepted practices for the administration of pharmaceutical preparations including specifically, but not exclusively, mucosal administration, oral consumption, ocular administration, subcutaneous injection, transdermal administration, etc.

Mucosal administration of the steroid includes such routes as buccal, endotracheal, nasal, pharyngeal, rectal, sublingual, vaginal, etc. For administration through the buccal/sublingual/pharyngeal/endotracheal mucosa, the steroid may be formulated as a gum, lozenge, spray, tablet or an inclusion complex such as cyclodextrin inclusion complexes. Nasal administration is conveniently conducted through the use of a sniffing power or nasal spray. For rectal and vaginal administration the steroid may be formulated as a cream, douch, enema or suppository.

Oral consumption of the steroid may be effected by incorporating the steroid into a food or drink, or formulating the steroid into a chewable or swallowable tablet.

Ocular administration may be effected by incorporating the steroid into a solution or suspension adapted for ocular application such as drops or sprays.

Subcutaneous administration involves incorporating the steroid into a pharmaceutically acceptable and injectable carrier.

For transdermal administration, the steroid may be conveniently incorporated into a lipophilic carrier and formulated as a topical creme or adhesive patch.

Dose Rate

The range of dosages and dose rates effective for achieving the desired biological properties and characteristics may be determined in accordance with standard industry practices. These ranges can be expected to differ depending upon whether the desired response is weight maintenance or weight loss of an average weight, overweight or obese subject.

Testing Protocol

Thermogenic Activity
(Production of Mitochondrial Glycerol-3-Phosphate Dehydrogenase and Cytosolic Malic Enzymes)
Administration of Steroid Male Sprague Dawley rats weighing 125–150 grams were obtained from Sasco Inc. of Oregon, Wis. The rats were allowed free access to water and Purina Rat Chow™ pellets. The steroids were administered orally (combined with the Purina Rat Chow) or intraperitoneally at a known concentration or dose for six days.

Preparation of Liver

Mitochondria and Cytosol Fractions

The rats were sacrificed on day seven. The livers were (i) excised, (ii) placed in 10 ml of a buffer solution consisting of 250 mM mannitol, 70 mM sucrose, and 3 mM Hepes (hereinafter MSH buffer solution) at pH 7.4, (iii) weighted, (iv) removed from the MSH buffer solution, (v) minced with scissors, (vi) washed with additional MSH buffer solution, (vii) suspended in MSH buffer solution at a ratio of 1 gram minced liver to 5 ml MSH buffer solution, and (viii) homogenized with a Potter-Elvehjem rotary homogenizer.

A Mitochondria fraction was prepared by the method described in Johnson, D. and Lardy, H. A., *Methods Enzymology*, Vol. 10, pp. 94–96 (1967) which is hereby incorporated by reference. Briefly, the liver homogenate was centrifuged in a Beckman Model J2–21 centrifuge equipped with a JA-20 rotor at 750 g for 10 minutes and the resulting supernatant solution centrifuged at 15,000 g from an additional 10 minutes to form mitochondrial pellets. The resulting mitochondrial pellets were washed twice with MSH buffer solution, resuspended in 0.8 to 1 ml of a 35 wt% aqueous glycerol solution, and stored at $-70°$ C.

A Cytosolic fraction was obtained by recentrifuging the previously centrifuged supernatant solution at 100,000 g for 30 minutes in a Beckman Model L2 ultracentrifuge equipped with a type 40 rotor. The resultant secondary supernatant solution was stored at $-70°$ C.

Protein concentrations in the resultant preparations were determined by the Biuret method described in Layne E., *Methods Enzymology*, Vol. 3, pp. 450–451 (1957) which is hereby incorporated by reference. Briefly, the protein concentrations were determined by treating a dilute solution of the preparation to be tested with copper tartrate solution and measuring the optical density at a wavelength of 540 nm.

Mitochondrial G3P-DH and

Cytosolic Malic Enzyme Assays

Mitochondrial Glycerophosphate dehydrogenase (G3P-DH) activity was measured by the method described in Wernette, M. E., Ochs, R. S., and Lardy, H. A., *J. Biol. Chem.*, Vol. 256, pp. 12767–12771 (1981), which is a modified version of the method described in Gardner, R. S., *Anal. Biochem.*, Vol. 59, pp. 272–276 (1974). Both references are hereby incorporated by reference. Briefly, aliquots of the previously prepared mitochondria suspensions added to test tubes containing 0.4 m. of an aqueous solution of 50 mM sn-glycerol-3-phosphate, 50 mM potassium phosphate (pH 7.0), 1 mM KCN, and 0.2% p-iodonitrotetrazolium violet and incubated for 30 min at $37°$ C. The incubating mitochondria were continuously agitated during the incubation period by a Dubnoff Shaker™ at 100 cycles/min. Incubation was ceased by the addition of 0.6 ml of 1 M acetic acid to the test tube.

The iodoformazan formed during the incubation period was extracted by adding 2 ml of ethyl acetate to the test tube, mixing thoroughly, and then decanting the ethyl acetate containing the iodoformazan from the test tube. The optical densities of the iodoformazan-containing ethyl acetate layers were read at a wavelength of 490 nm by means of an On Line Instrument Systems, Model 3820 Data System, Spectrophotometry, Cary-15, Version 4.08. An extinction coefficient value of $2.01 \times 10^4/(M \cdot cm)$ for the iodoformazan product in ethyl acetate was used to calculate enzyme activities.

Cytosolic malic enzyme activity was measured in accordance with the method described in Hsu, R. Y. and Lardy, H. A., *Methods Enzymol.*, Vol. 8, pp. 230–235 (1967). Briefly, aliquots of the previously prepared cytosol-containing secondary supernatant were added to test tubes containing 1 ml of an aqueous solution of 0.8 mM malate, 67 mM triethanolamine of buffer (pH 7.4), 4 mM $MnCl_2$, and 0.2 mM NADP and incubated for 3 min at $26°$ C. The incubating cytosol aliquots were continuously agitated during the incubation period by a Dubnoff Shaker™ at 100 cycles/min. Optical density of the incubating cytosol aliquots was measured at ½ and 2 minutes into the incubating period with an On Line Instrument Systems, Model 3820 Data System, Spectrophotometry, Cary x15, Version 4.08 at a wavelength of 340 nm. Malic enzyme activity was calculated as the rate of change in optical density.

Experimental

Example 1

Thermogenic Effect (G3P-DH and Malic Enzyme Activity of

Δ5 Androstene-3β-hemisuccinate-17-one)

The thermogenic activity of Δ5 Androstene-3β-hemisuccinate-17-one was determined in accordance with the testing protocol set forth herein. Test results are set forth below in Tables T1—1 and T1-2. The control and test animals in each test group were purchased together and the control animals fed the stock diet ad libitum without steroid supplementation.

TABLE 1-1

| # of Rats | Wt % Steroid in Diet | G3P-DH Activity | % Control | Malic Enzyme Activity | % Control |
|---|---|---|---|---|---|
| 3 | Zero (Control) | 4.7 | 100 | 18.7 | 100 |
| 2 | 0.059 | 8.2 | 174 | 63.2 | 338 |

TABLE 1-2

| # of Rats | Wt % Steroid in Diet | G3P-DH Activity | % Control | Malic Enzyme Activity | % Control |
|---|---|---|---|---|---|
| 3 | Zero (Control) | 3.7 | 100 | 15.6 | 100 |
| 2 | 0.059 | 8.8 | 236 | 65.6 | 420 |

Example 2

Thermogenic Effect (G3P-DH and Malic Enzyme Activity of

Δ5 Androstene-3β-propionate-17-one)

The thermogenic activity of Δ5 Androstene-3β-propionate-17-one was determined in accordance with the testing protocol set forth herein. Test results are set forth below in Tables T2-1, T2—2 and T2-3. The control and test animals in each test group were purchased together and the control animals fed the stock diet ad libitum without steroid supplementation.

TABLE 2-1

| # of Rats | Wt % Steroid in Diet | G3P-DH Activity | % Control | Malic Enzyme Activity | % Control |
|---|---|---|---|---|---|
| 3 | Zero (Control) | 3.5 | 100 | 21.9 | 100 |
| 2 | 0.052 | 7.2 | 206 | 66.2 | 302 |

TABLE 2-2

| # of Rats | Wt % Steroid in Diet | G3P-DH Activity | G3P-DH % Control | Malic Enzyme Activity | Malic Enzyme % Control |
|---|---|---|---|---|---|
| 3 | Zero (Control) | 4.4 | 100 | 27.7 | 100 |
| 2 | 0.052 | 8.4 | 191 | 113 | 408 |

TABLE 2-3

| # of Rats | Wt % Steroid in Diet | G3P-DH Activity | G3P-DH % Control | Malic Enzyme Activity | Malic Enzyme % Control |
|---|---|---|---|---|---|
| 3 | Zero (Control) | 3.1 | 100 | 29.5 | 100 |
| 2 | 0.060 | 8.6 | 277 | 80.6 | 273 |

Example 3
Thermogenic Effect
(G3P-DH and Malic Enzyme Activity of
Δ5 Androstene-3β-butyrate-17-one)

The thermogenic activity of Δ5 Androstene-3β-butyrate-17-one was determined in accordance with the testing protocol set forth herein. Test results are set forth below in Tables T3-1 and T3-2. The control and test animals in each test group were purchased together and the control animals fed the stock diet ad libitum without steroid supplementation.

TABLE 3-1

| # of Rats | Wt % Steroid in Diet | G3P-DH Activity | G3P-DH % Control | Malic Enzyme Activity | Malic Enzyme % Control |
|---|---|---|---|---|---|
| 3 | Zero (Control) | 6.0 | 100 | 22.7 | 100 |
| 3 | 0.062 | 7.5 | 125 | 34.1 | 150 |

TABLE 3-2

| # of Rats | Wt % Steroid in Diet | G3P-DH Activity | G3P-DH % Control | Malic Enzyme Activity | Malic Enzyme % Control |
|---|---|---|---|---|---|
| 2 | Zero (Control) | 4.7 | 100 | 30.3 | 100 |
| 2 | 0.062 | 11.8 | 251 | 80.5 | 266 |

Example 4
Thermogenic Effect
(G3P-DH and Malic Enzyme Activity of
Δ5 Androstene-3β-laurate-17-one)

The thermogenic activity of Δ5 Androstene-3β-laurate-17-one was determined in accordance with the testing protocol set forth herein. Test results are set forth below in Tables T4-1 and T4-2. The control and test animals in each test group were purchased together and the control animals fed the stock diet ad libitum without steroid supplementation.

TABLE 4-1

| # of Rats | Wt % Steroid in Diet | G3P-DH Activity | G3P-DH % Control | Malic Enzyme Activity | Malic Enzyme % Control |
|---|---|---|---|---|---|
| 3 | Zero (Control) | 3.5 | 100 | 31.5 | 100 |
| 3 | 0.0715 | 5.6 | 159 | 73.6 | 234 |

TABLE 4-2

| # of Rats | Wt % Steroid in Diet | G3P-DH Activity | G3P-DH % Control | Malic Enzyme Activity | Malic Enzyme % Control |
|---|---|---|---|---|---|
| 2 | Zero (Control) | 4.6 | 100 | 27.7 | 100 |
| 2 | 0.082 | 7.4 | 161 | 52.0 | 188 |

Example 5
Thermogenic Effect
(G3P-DH and Malic Enzyme Activity of
Δ5 Androstene-3β-palmitate-17-one)

The thermogenic activity of Δ5 Androstene-3β-palmitate-17-one was determined in accordance with the testing protocol set forth herein. Test results are set forth below in Tables T5-1 and T5-2. The control and test animals in each test group were purchased together and the control animals fed the stock diet ad libitum without steroid supplementation.

TABLE 5-1

| # of Rats | Wt % Steroid in Diet | G3P-DH Activity | G3P-DH % Control | Malic Enzyme Activity | Malic Enzyme % Control |
|---|---|---|---|---|---|
| 3 | Zero (Control) | 3.5 | 100 | 31.5 | 100 |
| 3 | 0.0715 | 6.9 | 198 | 68.2 | 217 |

TABLE 5-2

| # of Rats | Wt % Steroid in Diet | G3P-DH Activity | G3P-DH % Control | Malic Enzyme Activity | Malic Enzyme % Control |
|---|---|---|---|---|---|
| 2 | Zero (Control) | 4.6 | 100 | 27.7 | 100 |
| 2 | 0.082 | 8.7 | 189 | 72.5 | 262 |

Comparative Example 6
Thermogenic Effect
(G3P-DH and Malic Enzyme Activity of
Δ5 Androstene-3β-isobutyrate-17-one)

The thermnogenic activity of Δ5 Androstene-3β-isobutyrate-17-one was determined in accordance with the testing protocol set forth herein. Test results are set forth below in Tables T4-1 and T4-2. The control and test animals in each test group were purchased together and the control animals fed the stock diet ad libitum without steroid supplementation.

TABLE 6-1

| # of Rats | Wt % Steroid in Diet | G3P-DH Activity | G3P-DH % Control | Malic Enzyme Activity | Malic Enzyme % Control |
|---|---|---|---|---|---|
| 3 | Zero (Control) | 5.9 | 100 | 29.5 | 100 |
| 3 | 0.062 | 5.9 | 100 | 34.0 | 115 |

TABLE 6-2

| # of Rats | Wt % Steroid in Diet | G3P-DH Activity | G3P-DH % Control | Malic Enzyme Activity | Malic Enzyme % Control |
|---|---|---|---|---|---|
| 3 | Zero (Control) | 5.0 | 100 | 29.6 | 100 |
| 3 | 0.062 | 4.7 | 94 | 40.4 | 136 |

A comparison of the data set forth in Table T6-1 and T6-2 for Δ5 Androstene-3βisobutyrate-17-one (a branched $C_4$ carboxylate) and the data set forth in Tables T3-1 and T3-2 for Δ5 Androstene-3β-butyrate-17-one (an unbranched $C_4$ carboxylate), suggests that the incorporation of a branched moiety at the 3βposition hinders the thermogenic functionality of the steroid.

I claim:

1. A method for averting weight gain, comprising administering to a subject prone to weight gain an effective weight gain preventative amount of a biologically active Δ5 Androstene-3β-carboxylate-17-one steroid wherein the carboxylate is an ester of a saturated, unbranched $C_{2-24}$ monocarboxylic acid.

2. A method for promoting weight loss, comprising administering to a subject in need of such treatment an effective weight reduction promoting amount of a biologically active Δ5 Androstene-3β-carboxylate-17-one steroid wherein the carboxylate is an ester of a saturated, unbranched $C_{2-24}$ monocarboxylic acid.

3. A method of treating obesity, comprising administering to an obese subject a therapeutic amount of a biologically active Δ5 Androstene-3β-carboxylate-17-one steroid wherein the carboxylate is an ester of a saturated, unbranched $C_{2-24}$ monocarboxylic.

4. The method of claim 1 wherein the saturated, unbranched $C_{2-24}$ carboxylic acids are saturated, unbranched, short-chain fatty acids.

5. The method of claim 1 wherein the saturated, unbranched $C_{2-24}$ carboxylic acids are saturated, unbranched, long-chain fatty acids.

6. The method of claim 2 wherein the saturated, unbranched $C_{2-24}$ carboxylic acids are saturated, unbranched, short-chain fatty acids.

7. The method of claim 2 wherein the saturated, unbranched $C_{2-24}$ carboxylic acids are saturated, unbranched, long-chain fatty acids.

8. The method of claim 3 wherein the saturated, unbranched $C_{2-24}$ carboxylic acids are saturated, unbranched, short-chain fatty acids.

9. The method of claim 3 wherein the saturated, unbranched $C_{2-24}$ carboxylic acids are saturated, unbranched, long-chain fatty acids.

10. A method for averting weight gain, comprising administering to a subject prone to weight gain an effective weight gain preventative amount of Δ5 Androstene-3β-hemisuccinate-17-one.

11. A method for promoting weight loss, comprising administering to a subject in need of such treatment an effective weight reduction promoting amount of Δ5 Androstene-3β-hemisuccinate-17-one.

12. A method of treating obesity, comprising administering to an obese subject a therapeutic amount of Δ5 Androstene-3β-hemisuccinate-17-one.

13. The method of claim 10 wherein the administration of Δ5 Androstene-3β-hemisuccinate-17-one comprises the administration of substantially pure Δ5 Androstene-3β-hemisuccinate-17-one.

14. The method of claim 11 wherein the administration of Δ5 Androstene-3β-hemisuccinate-17-one comprises the administration of substantially pure Δ5 Androstene-3β-hemisuccinate-17-one.

15. The method of claim 12 wherein the administration of Δ5 Androstene-3β-hemisuccinate-17-one comprises the administration of substantially pure Δ5 Androstene-3β-hemisuccinate-17-one.

16. A method for averting weight gain, comprising administering to a subject prone to weight gain an effective weight gain preventative amount of Δ5 Androstene-3β-propionate-17-one.

17. A method for promoting weight loss, comprising administering to a subject in need of such treatment an effective weight reduction promoting amount Δ5 Androstene-3β-propionate-17-one.

18. A method of treating obesity, comprising administering to an obese subject a therapeutic amount of Δ5 Androstene-3β-propionate-17-one.

19. The method of claim 16 wherein the administration of Δ5 Androstene-3β-propionate-17-one comprises the administration of substantially pure Δ5 Androstene-3β-propionate-17-one.

20. The method of claim 17 wherein the administration of Δ5 Androstene-3β-propionate-17-one comprises the administration of substantially pure Δ5 Androstene-3β-propionate-17-one.

21. The method of claim 18 wherein the administration of Δ5 Androstene-3β-propionate-17-one comprises the administration of substantially pure Δ5 Androstene-3β-propionate-17-one.

22. A method for averting weight gain, comprising administering to a subject prone to weight gain an effective weight gain preventative amount of Δ5 Androstene-3β-butyrate-17-one.

23. A method for promoting weight loss, comprising administering to a subject in need of such treatment an effective weight reduction promoting amount Δ5 Androstene-3β-butyrate-17-one.

24. A method of treating obesity, comprising administering to an obese subject a therapeutic amount of Δ5 Androstene-3β-butyrate-17-one.

25. The method of claim 22 wherein the administration of Δ5 Androstene-3β-butyrate-17-one comprises the administration of substantially pure Δ5 Androstene-3β-butyrate-17-one.

26. The method of claim 23 wherein the administration of Δ5 Androstene-3β-butyrate-17-one comprises the administration of substantially pure Δ5 Androstene-3β-butyrate-17-one.

27. The method of claim 24 wherein the administration of Δ5 Androstene-3β-butyrate-17-one comprises the administration of substantially pure Δ5 Androstene-3β-butyrate-17-one.

28. A method for averting weight gain, comprising administering to a subject prone to weight gain an effective weight gain preventative amount of Δ5 Androstene-3β-laurate-17-one.

29. A method for promoting weight loss, comprising administering to a subject in need of such treatment an effective weight reduction promoting amount Δ5 Androstene-3β-laurate-17-one.

30. A method of treating obesity, comprising administering to an obese subject a therapeutic amount of Δ5 Androstene-3β-laurate-17-one.

31. The method of claim 28 wherein the administration of Δ5 Androstene-3β-laurate-17-one comprises the administration of substantially pure Δ5 Androstene-3β-laurate-17-one.

32. The method of claim 29 wherein the administration of Δ5 Androstene-3β-laurate-17-one comprises the administration of substantially pure Δ5 Androstene-3β-laurate-17-one.

33. The method of claim 30 wherein the administration of Δ5 Androstene-3β-laurate-17-one comprises the administration of substantially pure Δ5 Androstene-3β-laurate-17-one.

34. A method for averting weight gain, comprising administering to a subject prone to weight gain an effective weight gain preventative amount of Δ5 Androstene-3β-palmitate-17-one.

35. A method for promoting weight loss, comprising administering to a subject in need of such treatment an effective weight reduction promoting amount Δ5 Androstene-3β-palmitate-7-one.

36. A method of treating obesity, comprising administering to an obese subject a therapeutic amount of Δ5 Androstene-3β-palmitate-7-one.

37. The method of claim 34 wherein the administration of Δ5 Androstene-3β-palmitate-7-one comprises the administration of substantially pure Δ5 Androstene-3β-palmitate-7-one.

38. The method of claim 35 wherein the administration of Δ5 Androstene-3β-palmitate-7-one comprises the administration of substantially pure Δ5 Androstene-3β-palmitate-7-one.

39. The method of claim 36 wherein the administration of Δ5 Androstene-3β-palmitate-7-one comprises the administration of substantially pure Δ5 Androstene-3β-palmitate-7-one.

* * * * *

UNITED STATES PATENT AND TRADEMARK OFFICE
CERTIFICATE OF CORRECTION

PATENT NO. : 5,807,848
DATED : September 15, 1998
INVENTOR(S) : Lardy

It is certified that error appears in the above-identified patent and that said Letters Patent is hereby corrected as shown below: Title page, item [54]

Title, replace "DEHYDROEPEIANDROSTERONE" with -- DEHYDROEPIANDROSTERONE --

Col. 1, Line 1, replace "DEHYDROEPEIANDROSTERONE" with -- DEHYDROEPIANDROSTERONE --

Col. 4, Line 11, replace "Cary x 15," with -- Cary - 15, --

Col. 7, Line 6, replace "moiety at the 3β position" with -- moiety at the 3β position --

Signed and Sealed this

Sixteenth Day of November, 1999

Attest:

Q. TODD DICKINSON

*Attesting Officer*  *Acting Commissioner of Patents and Trademarks*